(12) United States Patent
Morgan et al.

(10) Patent No.: US 7,783,366 B1
(45) Date of Patent: Aug. 24, 2010

(54) LEAD FOR AV NODAL VAGAL STIMULATION THROUGH AN EPICARDIAL FAT PAD

(75) Inventors: Kevin L. Morgan, Simi Valley, CA (US); Todor N. Mazgalev, Pepper Pike, OH (US)

(73) Assignees: Pacesetter, Inc., Sylmar, CA (US); The Cleveland Clinic Foundation, Cleveland, OH (US)

( * ) Notice: Subject to any disclaimer, the term of this patent is extended or adjusted under 35 U.S.C. 154(b) by 809 days.

(21) Appl. No.: 11/677,966

(22) Filed: Feb. 22, 2007

(51) Int. Cl.
*A61N 1/05* (2006.01)
(52) U.S. Cl. .................. 607/129; 607/130
(58) Field of Classification Search .......... 607/129, 607/130
See application file for complete search history.

(56) References Cited

U.S. PATENT DOCUMENTS

| 7,212,871 B1* | 5/2007 | Morgan ............... 607/129 |
| 2003/0078623 A1 | 4/2003 | Weinberg et al. |
| 2004/0176830 A1* | 9/2004 | Fang .................. 607/129 |
| 2004/0199210 A1 | 10/2004 | Shelchuk |
| 2005/0065553 A1 | 3/2005 | Ben Ezra et al. |

FOREIGN PATENT DOCUMENTS

| EP | 1304135 A2 | 4/2003 |
| EP | 1304135 A3 | 4/2003 |
| EP | 1486232 A2 | 12/2004 |
| EP | 1486232 A3 | 12/2004 |

OTHER PUBLICATIONS

Tabata, Tomotsugu et al., "Determinants of LV diastolic function during atrial fibrillation: beat-to-beat analysis in acute dog experiments," Am J Physiol Heart Circ Physiol 286: H145-H132, 2004.
Zhang, Youhua MD et al., "Chronic Atrioventricular Nodal Vagal Stimulation—First Evidence for Long-Term Ventricular Rate Control in Canine Atrial Fibrillation Model," Circulation. 2005; 112: 2904-2911.

* cited by examiner

*Primary Examiner*—Carl H. Layno
*Assistant Examiner*—Jon-Eric C. Morales (57) ABSTRACT

A medical electrical lead for conducting electrical signals between an electrical stimulator and a heart site includes a lead body extending from a distal non-conductive disk member to a proximal connector for attachment to the stimulator, first and second spaced electrodes protruding from the disk member for puncturing engagement with the epicardial surface of the heart in the region of an AVN fat pad containing ganglia which extend to the AV node providing an electrical connection between the atrium and the ventricle, a first conductor extending from the first electrode to a first terminal of the connector, and a second conductor extending from the second electrode to a second terminal of the connector such that electrical current from the electrical stimulator is caused to flow through the ganglia between the first and second electrodes to stimulate the AV node to control ventricular rate in the presence of atrial fibrillation.

13 Claims, 6 Drawing Sheets

LEAD FOR AV NODAL VAGAL STIMULATION THROUGH AN EPICARDIAL FAT PAD

TECHNICAL FIELD

The present invention generally relates to stimulation leads for use with implantable cardiac stimulation devices and, more particularly, to a technique and lead for controlling ventricular rate in the presence of atrial fibrillation.

BACKGROUND

A patient who is suffering from atrial fibrillation can experience a ventricular rate (bpm) that is higher than normal for that patient. This can result in adverse effects of left ventricular function. Some examples of these effects are diminished preload and contractility of the chambers due to shorter filling intervals. Atrial fibrillation (AF) is recognized as the most common clinically significant cardiac arrhythmia. Current data estimated that 2.3 million Americans have AF. Because the prevalence of AF increases with age and because of the aging population, the number of AF patients is estimated to increase 2.5-fold during the next 50 years.

Currently, there are two broad strategic treatment options for AF: rhythm control and rate control. Although rhythm control (restoring and maintaining the sinus rate) is thought to be ideal, it cannot be achieved or maintained in a large number of patients, rendering rate control (controlling ventricular rate while AF continues) the only realistic long-term solution in a majority of patients. Recent clinical trials have demonstrated that rate control is at least as good as rhythm control for most patients with AF. Thus, rate control can be considered a "primary approach" in treating these AF patients.

The strategy of rate control during AF essentially deals with efforts to utilize and adjust the filtering properties of the atrioventricular node (AVN) because the AVN is the only normal structure responsible for the conduction of atrial impulses to the ventricles. Drug therapy (calcium channel antagonists, β-blockers, and digitalis) is the most common approach in rate control. However, drug therapy is not effective in some patients and may not be well tolerated in others because of side effects. These various drugs have been used to slow down the heart rate by lengthening the refractory period of the AV node. Although this therapy sounds reasonable, one side effect is that in many cases the patient is required to take combinations of drugs to control the ventricular rate, and another is that patients who have intermittent episodes of atrial fibrillation can experience excessive bradycardia due to inappropriate drug induced inhibitions of the AV node when the atrium is in sinus rhythm.

AVN modification can be used to control the ventricular rate. Because of the limited success rate and high probability of complete AV block, it is currently recommended only when AVN ablation with pacemaker implantation is intended. The latter option results in a lifelong pacemaker dependency. In addition, there are hemodynamic drawbacks because of the retrograde ventricular contraction. Recently, lesions encircling rather than destroying the AVN were shown to result in acceptable junctional escape rhythm. However, this technique needs further refinements and verification.

Recently, a novel strategy, selective AVN vagal stimulation (AVN-VS), has emerged for rate control during AF. It has been demonstrated that AVN-VS could be used to achieve desired predetermined ventricular rate slowing with improved hemodynamics in acute experiments. Moreover, ventricular rate slowing by AVN-VS provided better hemodynamic benefit than AVN ablation and right ventricular pacing. Further, it has also been demonstrated that beneficial long-term ventricular rate slowing during AF can be achieved by implantation of a nerve stimulator attached to the epicardial AVN fat pad and is an attractive alternative to other methods of rate control.

It was in light of the foregoing that the present invention was conceived and has now been reduced to practice.

SUMMARY OF THE INVENTION

A medical electrical lead for conducting electrical signals between an electrical stimulator and a heart site includes a lead body extending from a distal non-conductive disk member to a proximal connector for attachment to the stimulator, first and second spaced electrodes protruding from the disk member for puncturing engagement with the epicardial surface of the heart in the region of an AVN fat pad containing ganglia which extend to the AV node providing an electrical connection between the atrium and the ventricle, a first conductor extending from the first electrode to a first terminal of the connector, and a second conductor extending from the second electrode to a second terminal of the connector such that electrical current from the electrical stimulator is caused to flow through the ganglia between the first and second electrodes to stimulate the AV node to control ventricular rate in the presence of atrial fibrillation.

This approach for controlling the ventricular rate by selectively stimulating the AV node by way of the vagal nerve through an epicardial fat pad requires a specialized lead design. This specialized lead is specifically designed for placement on the epicardial surface of the heart in the fat pad region to apply stimulation to the AV node. The distal end of the lead has a flat disk feature. In one design, this disk has four pins extending transversely from the flat disk and these pins are the electrodes for delivering the electrical impulses to the fat pad region of the heart.

There are two slightly different versions of the lead design. One design is a lead that has a distal pad with four pins protruding from the pad. These four pins are divided into two sets of two pins. Each set is then connected to either the cathode conductor (IS-1 pin) or to the anode conductor (IS-1 ring). The second design has a distal pad with four transversely protruding pins as mentioned above. The variation of this distal pad is that each set of two pins has an added intermediate electrode to increase the surface area of each electrode and thereby reduce the impedance of the electrodes. This design may also have a bifurcation toward the proximal end of the lead which splits off to an IS-1 connector and a DF-1 connector. These connectors are designed to connect into the ports of an ICD. The lead in this configuration is not designed for defibrillation of the heart. However, a lead designed to defibrillate is conceivable and is presented in this disclosure.

The fat pad lead is constructed from a biocompatible material such as silicone or polyurethane. An electrically non-conductive disk shaped pad is located on the distal end of the lead and supports pins which are electrodes protruding transversely from the pad. Multiples of pins may protrude from the pad but there must be at least two pins which are divided into positive and negative electrical poles. Conductors are connected to each pole and these conductors are placed inside the lead body which is made of the biocompatible material. The proximal end of the lead in one configuration is terminated in an IS-1 connector. The second lead configuration has a bifurcation on the lead body that splits the conductors into two different connectors. One connector may be of an IS-1 design and the other connector may be of a DF-1 design, these connectors being arranged to fit into an ICD header provided to receive such lead connections.

Another lead configuration provides for an increased surface area on each pole. This increase surface area is in the form of a plate like surface located intermediate the two anode pins and the two cathode pins. This plate like surface can also have a curved shape so as to improve the tissue contact achieved by that electrode.

A primary feature of the invention, then, is the provision of a novel technique and lead for controlling ventricular rate in the presence of atrial fibrillation.

Another feature of the present invention is the provision of such a novel technique and lead which operates for vagal nerve stimulation through the fat pad region of the heart.

Still another feature of the present invention is the provision of such a novel technique and lead which provides the ability to control the ventricular rate of the heart through the AV node from the fat pad region of the heart.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
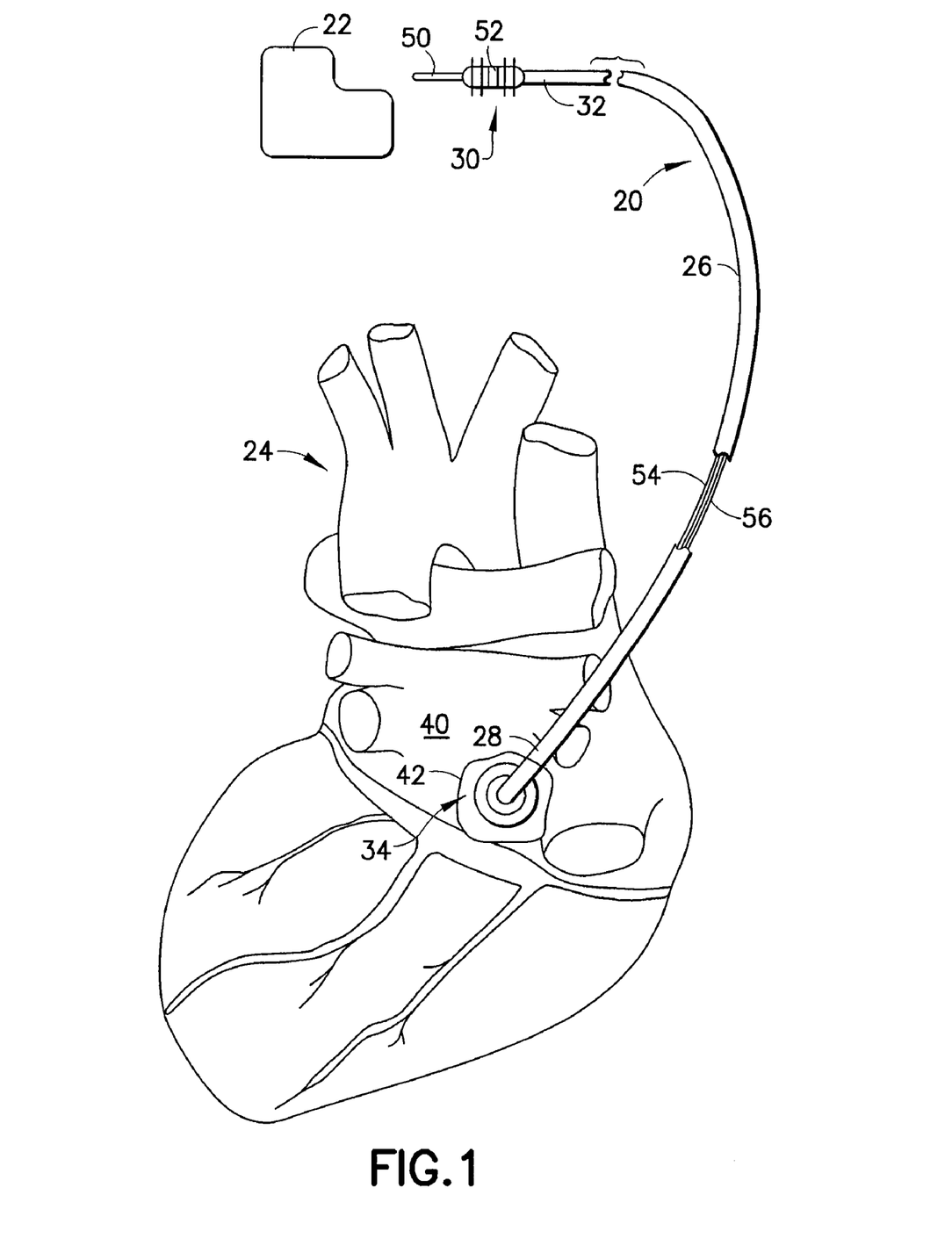
FIG. 1 is a diagrammatic perspective view illustrating an implanted lead system for providing electrical stimulation of a heart employing an implanted lead embodying the present invention.

Refer now to the drawings and, initially, to FIG. 1 in which is shown a diagrammatic perspective view of a medical electrical epicardial lead 20 incorporating features of the present invention for use in association with an electrical stimulator 22 such as a pacemaker or defibrillator providing electrical stimulation to a heart 24. Although the present invention will be described with reference to the embodiments shown in the drawings, it should be understood that the present invention can be embodied in many alternate forms or embodiments. In addition, any suitable size, shape or type of elements or materials could be used.

Figure 2:
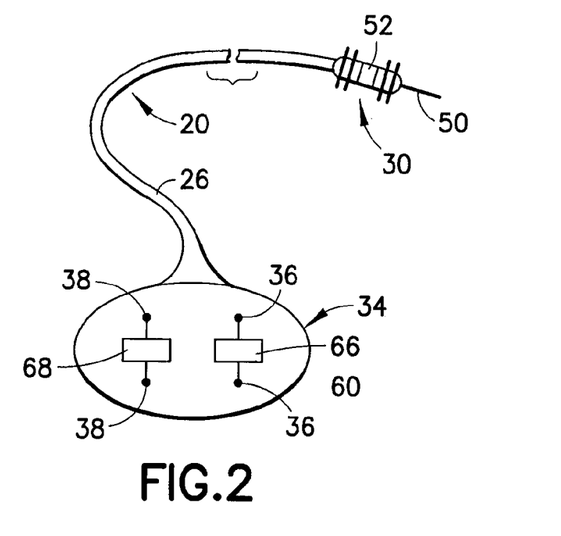
FIG. 2 is a bottom plan view of a lead utilizing a distal disk member embodying the present invention.

The lead 20 is adapted to conduct electrical stimulation from the electrical stimulator 22, which may be, alternatively and selectively, implantable or external to a site of the heart 24 and to conduct electrical signals of the heart from the site to the stimulator. The lead 20 includes an elongated lead body 26 extending from a lead body distal end 28 to a connector 30 at the lead body proximal end 32 for mechanical and electrical attachment to the electrical stimulator 22. An electrically non-conductive electrode head, or disk member, 34 is provided at the lead body distal end 28 and, viewing FIGS. 2 and 3, includes at least first and second parallel spaced apart electrodes 36, 38, respectively, fixed on the disk member and protruding therefrom for puncturing engagement with the epicardial surface 40 of the heart in the region of an AVN fat pad 42 containing ganglia 44 which extend to the AV node 46 (FIG. 4) providing an electrical connection between the atrium 47 and the ventricle 48. As illustrated, there is actually a pair of the electrodes 36, 38 and still more first and second electrodes could be provided, if desired.

A connector pin, or first, terminal 50, which may be a cathode pin, is electrically in common with the each of the first electrodes 36 at the distal end of the lead and a connector ring, or second terminal, 52, which may be an anode ring, is electrically in common with each of the second electrodes 38. A first conductor 54 (FIG. 1) extends within the lead body 26 from each first electrode 36 to the connector pin 50 and a second conductor 56 similarly extends within the lead body 26 from each second electrode 36 to the connector ring 52. Preferably, each electrode 36, 38 is elongated and extends to an angled tip end 54 (FIG. 3) for ease of penetration into the fat pad. Thus, when the disk member 34 is attached to the fat pad by way of the electrodes 36, 38, in the manner just described, electrical current can be transmitted from the electrical stimulator 22 through the ganglia 44 from the first electrode to the second electrode to stimulate the AV node 46 and this operation can be performed to control ventricular rate in the presence of atrial fibrillation.

Figure 3:
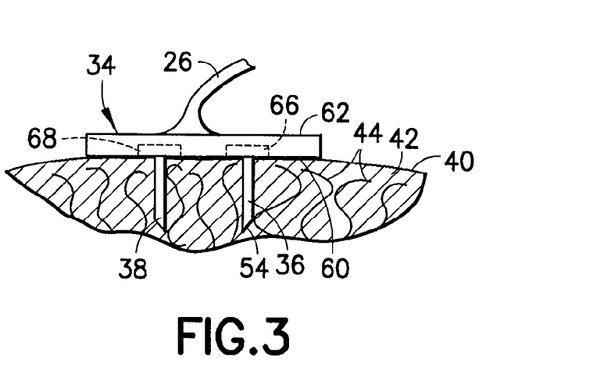
FIG. 3 is a side elevation view of the distal disk member of the invention as illustrated in FIG. 2 but implanted on an AVN fat pad of the epicardial surface of the heart.
Figure 3A:
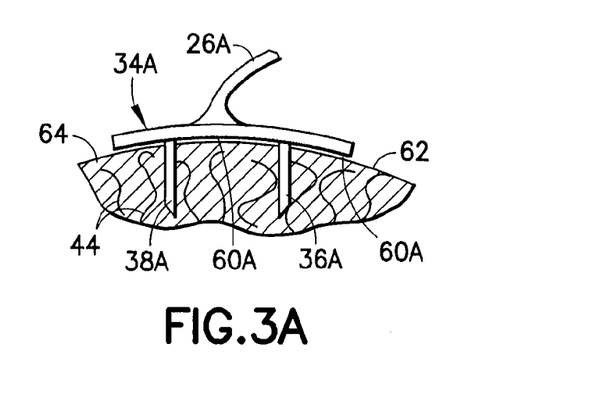
FIG. 3A is side elevation view, similar to FIG. 3, illustrating a modified distal disk member of the invention implanted on an AVN fat pad of the epicardial surface of the heart.
Figure 4:
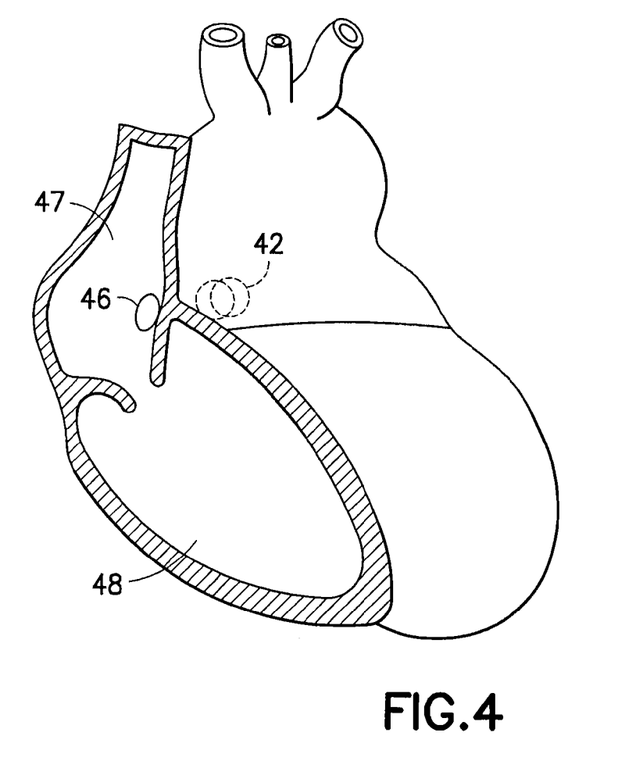
FIG. 4 is a perspective anterior view of the heart shown partly in section.

Other variations of the lead 20 just described are possible without changing its basic operation. For example, in one instance, the first and second electrodes may be of equal length while, in another instance, they may be of different lengths. Again, in one instance, as seen in FIG. 3, the disk member has a generally planar undersurface 60 from which the electrodes 36, 38 project in a substantially perpendicular manner. In another instance, viewing FIG. 3A, a modified disk member 34A is of either flexible or semi-rigid biocompatible material and has a contoured undersurface 60A so as to be engageable with a similarly contoured outer surface 62 of a bulbous AVN fat pad region 64 of the epicardial surface of the heart. In this instance, the electrodes 36, 38 would not be perpendicular to the undersurface 60A but would remain mutually parallel for ease of penetration into the fat pad. In still another instance, the disk member 34 has a generally planar undersurface 60 (FIG. 3) from which the plurality of the first and second electrodes project and includes at least one conductive plate 66 (FIGS. 2 and 3) mounted on the undersurface 60 and electrically in continuity with the plurality of the first electrodes 36 and at least one conductive plate 68 similarly mounted on the undersurface 60 and electrically in continuity with the plurality of the second electrodes 38. This construction serves to give flexibility to the surface area of each electrode. This allows the surface area of both electrodes to increase beyond that of electrodes 36, 38 or to vary the surface areas between the electrodes 36, 38 to optimize the impedance of the electrodes thereby improving the operation of the lead. In still another instance, it might be desirable for each of the electrodes 36, 38 to be coated with titanium nitride or platinum black for decreasing polarization effects.

Turn now to FIGS. 5A-5E and FIGS. 6A-6B for another embodiment of the invention. For this embodiment, a lead 70 includes an elongated lead body 72 is seen to extend from a lead body distal end 74 to a connector 76 at the lead body proximal end 78 for mechanical and electrical attachment to the electrical stimulator which is not illustrated in this series of drawings. The lead 70 further includes an electrically non-conductive disk member 80 at the lead body distal end 74, generally similar to the disk member 34 of the previous embodiment. The disk member 80 has an upper surface 82, a lower surface 84, an outer peripheral edge 86 between the upper surface and the lower surface, and a centrally located throughbore 88 extending between the upper surface and the lower surface.

Figure 5A:
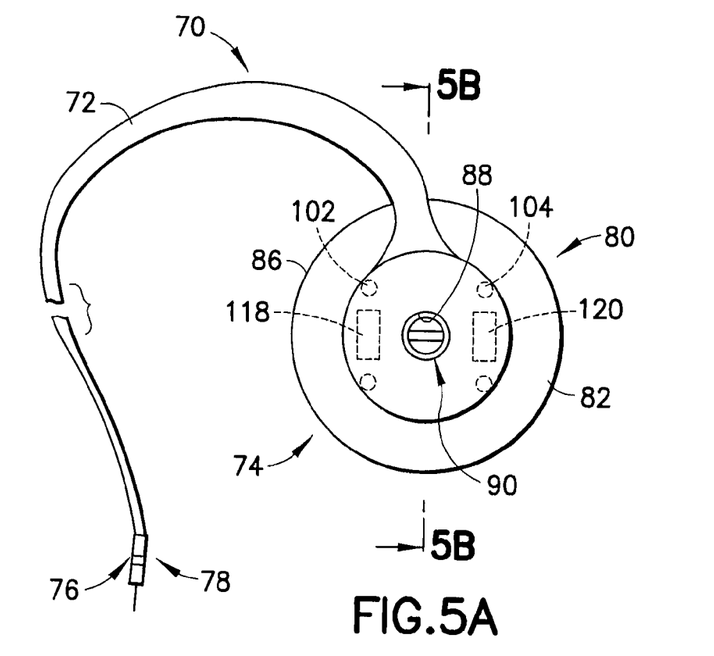
FIG. 5A is a top plan view of a lead utilizing a modified distal disk member embodying the present invention.
Figure 5B:
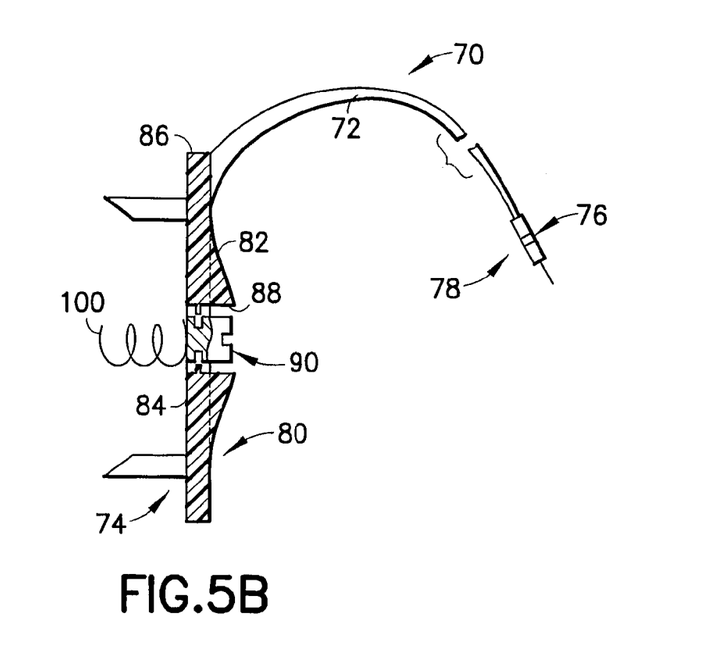
FIG. 5B is a cross section view taken generally along line 5B-5B in FIG. 5A.
Figure 5C:
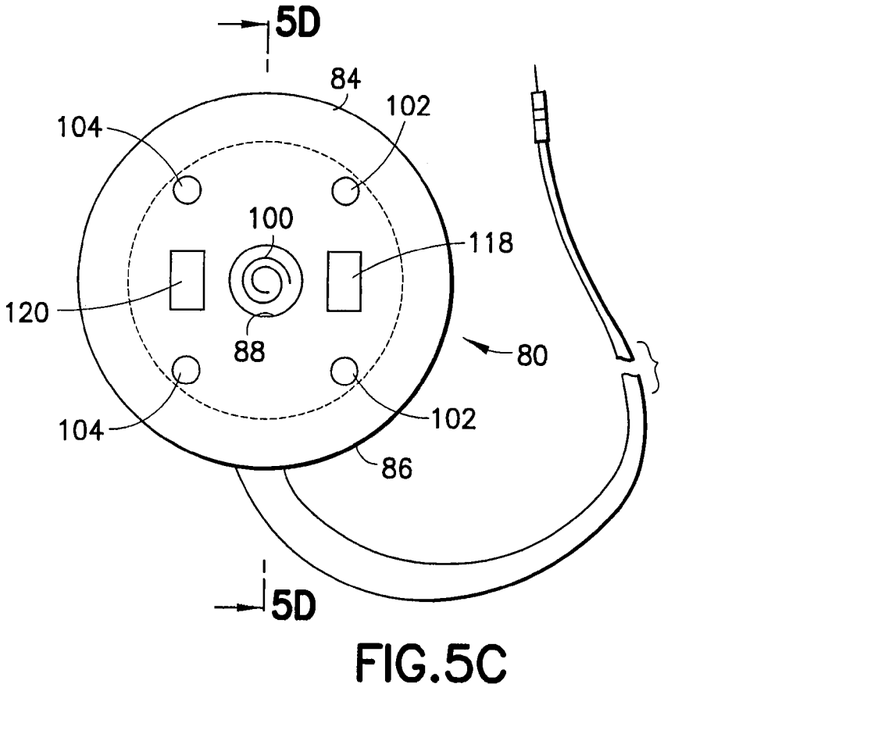
FIG. 5C is a bottom plan view of the modified lead illustrated in FIGS. 5A and 5B.
Figure 5D:
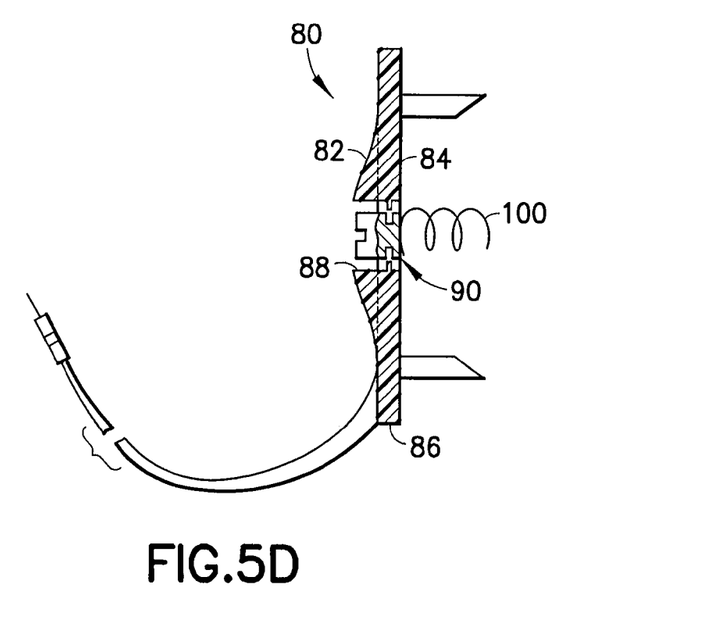
FIG. 5D is a cross section view taken generally along line 5D-5D in FIG. 5C.
Figure 5E:
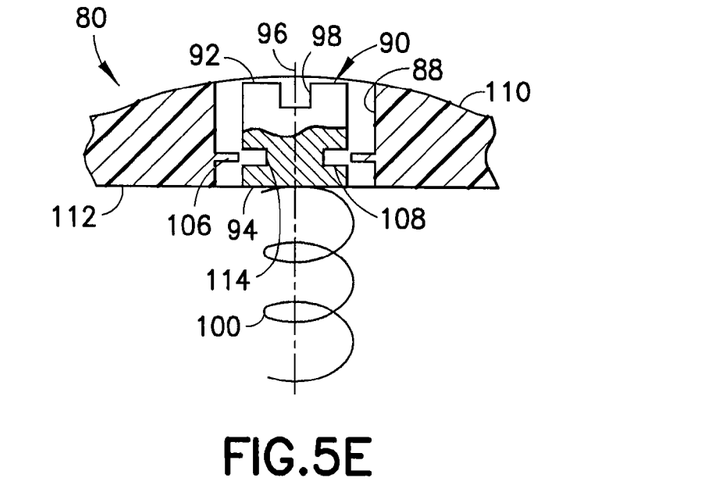
FIG. 5E is a detail cross section view to illustrate with greater clarity a portion of FIG. 5B.
Figure 6A:
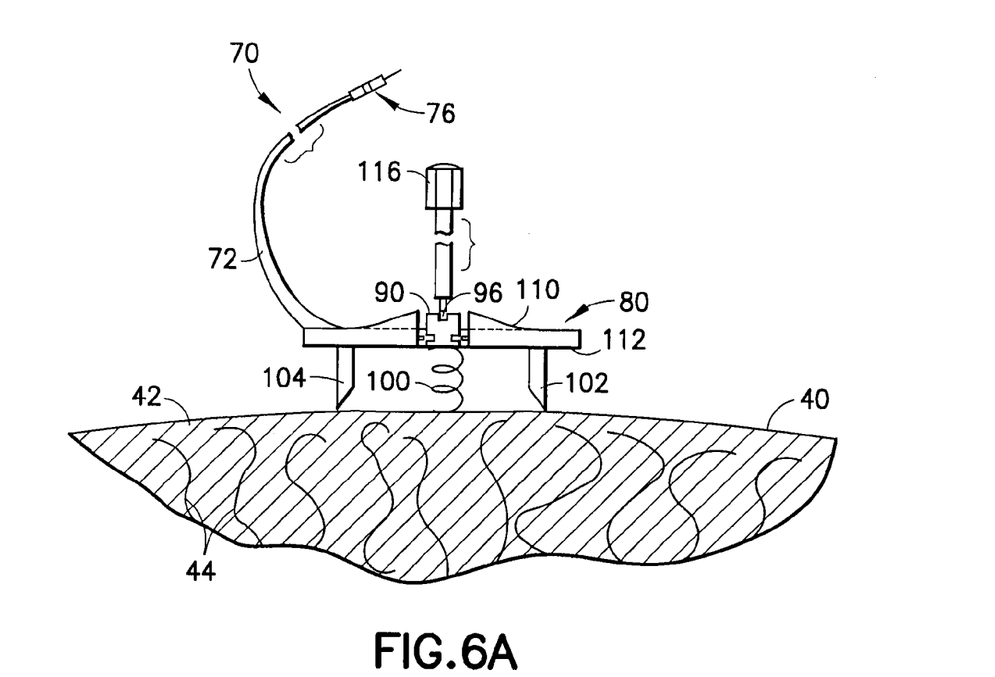
FIG. 6A is side elevation view, similar to FIG. 3 illustrating the modified distal disk member of the invention about to be implanted on an AVN fat pad of the epicardial surface of the heart.
Figure 6B:
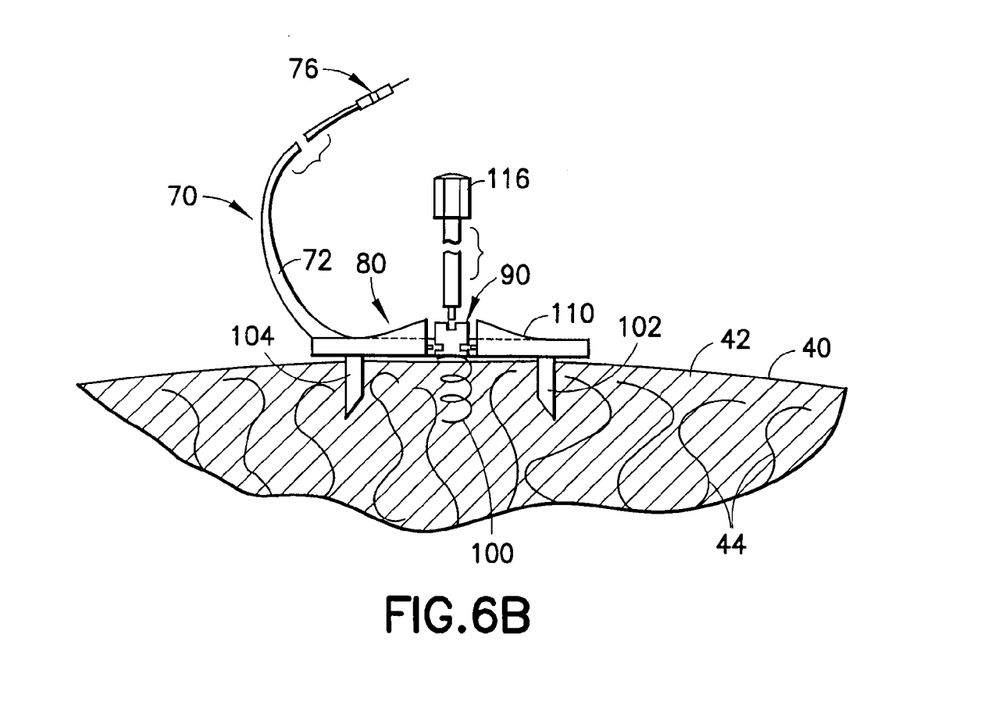
FIG. 6B is side elevation view, similar to FIG. 6A illustrating the modified distal disk member of the invention fully implanted on an AVN fat pad of the epicardial surface of the heart.

Viewing especially FIG. 5E, the disk member 80 includes a cylindrical helix driver 90 extending between a first end 92 and a second end 94 positioned in the throughbore 88 of the disk member. The helix driver 90 is rotatably mounted on the disk member 80 for rotation about a rotation axis 96 generally parallel with the first and second electrodes and having a tool reception feature 98 on the first end 92. A helical screw 100 fixed on the second end 94 (FIG. 5E) of the helix driver 90 projects away from the disk member 80 and is aligned with the rotation axis 96. Also, the helical screw 100 is laterally intermediate first and second electrodes 102, 104 (FIGS. 5B, 5C, and 5D).

As in the previous embodiment, the first and second electrodes 102, 104 are fixed on the disk member 80 and protrude transversely therefrom for puncturing engagement (FIGS. 6A and 6B) with the epicardial surface 40 of the heart 24 in the region of an AVN fat pad 42 containing ganglia 44 which extend to the AV node 46 (FIG. 4) providing an electrical connection between the atrium 47 and the ventricle 48. Turning back to FIG. 5E, for rotatably supporting the helix driver 90, a flexible annular flange 106 projects inwardly from the wall of the throughbore 88 toward the rotation axis 96 and is freely received by an annular groove 108 in the helix driver. To mount the helix driver 90 on the disk member 80, the helix driver is inserted, second end 94 first, into the throughbore 88, past an outer surface 110 toward an undersurface 112, and into engagement with the annular flange 106, pushing the annular flange aside until an inner rim 114 of the annular flange locates the annular groove 108 and the annular flange becomes freely captured in the annular groove. With this construction, rotation about the rotation axis 96 of a tool 116 (FIGS. 6A and 6B) such as a spade-tipped screwdriver engagable with the tool reception feature 98 causes rotation of the helix driver 90 and therefore of the helical screw 100 into the AVN fat pad 42 and draws the undersurface 112 of the disk member into conforming engagement with the outer surface of the AVN fat pad. Also, as in the previous embodiment, at least one conductive plate 118 is mounted on the undersurface 112 and electrically in continuity with the first electrodes 102 and at least one conductive plate 120 is mounted on the undersurface 112 and electrically in continuity with the second electrodes 104. Additionally, this embodiment may feature any or all of the other modifications found in the earlier embodiment.

While preferred embodiments of the invention have been disclosed in detail, it should be understood by those skilled in the art that various other modifications may be made to the illustrated embodiments without departing from the scope of the invention as described in the specification and defined in the appended claims.

What is claimed is:

1. A medical electrical lead adapted to conduct electrical signals from an implantable or external electrical stimulator to a site of the heart and to conduct electrical signals of the heart from the site to the implantable or external electrical stimulator comprising:
   an elongated lead body extending from a lead body distal end to a connector at the lead body proximal end for mechanical and electrical attachment to the electrical stimulator;
   an electrically non-conductive disk member at the lead body distal end;
   at least a first electrode fixed on the disk member and protruding therefrom for puncturing engagement with the epicardial surface of the heart in the region of an atrioventricular node (AVN) fat pad;
   at least a second electrode fixed on the disk member, spaced from the first electrode, and protruding therefrom for puncturing engagement with the epicardial surface of the heart in the region of the AVN fat pad;
   a first conductor extending from the first electrode to a first terminal of the connector; and
   a second conductor extending from the second electrode to a second terminal of the connector
   wherein the connector at the proximal end includes a cathode pin and an anode ring;
   wherein the first conductor extends between the first electrode and the cathode pin; and
   wherein the second conductor extends between the second electrode and the anode ring.

2. A medical electrical lead as set forth in claim 1 wherein the disk member includes a plurality of first parallel mutually spaced electrodes; and
   wherein the disk member includes a plurality of second parallel mutually spaced electrodes.

3. A medical electrical lead as set forth in claim 2 wherein the plurality of the first and second electrodes are of equal length.

4. A medical electrical lead as set forth in claim 2 wherein the plurality of the first and second electrodes are of different lengths.

5. A medical electrical lead as set forth in claim 2 wherein the disk member has a generally planar under surface from which the plurality of the first and second electrodes project.

6. A medical electrical lead as set forth in claim 5 wherein the plurality of the first and second electrodes are substantially perpendicular to the under surface from which they project.

7. A medical electrical lead as set forth in claim 2 wherein each of the first and second electrodes is coated with titanium nitride or platinum black for decreasing the polarization effects.

8. A medical electrical lead as set forth in claim 1 wherein the disk member is of flexible material and has a substantially planar undersurface capable of conforming engagement with a contoured outer surface of the AVN fat pad region of the epicardial surface of the heart.

9. A medical electrical lead as set forth in claim 1 including:
a helix driver rotatably mounted on the disk member; and
a helical screw fixed on the helix driver projecting away from the disk member in a direction generally parallel with, and intermediate, the first and second electrodes also for projecting engagement with the AVN fat pad;
whereby rotation of the helix driver and therefore of the helical screw into the AVN fat pad draws the disk member into conforming engagement with the outer surface of the AVN fat pad.

10. A medical electrical lead as set forth in claim 1
wherein the disk member has an upper surface, a lower surface, and an outer peripheral edge between the upper surface and the lower surface and a centrally located throughbore extending between the upper surface and the lower surface; and
including:
a cylindrical helix driver extending between a first end and a second end positioned in the throughbore of the disk member and rotatably mounted on the disk member for rotation about a rotation axis generally parallel with the first and second electrodes and having a tool reception feature on the first end; and
a helical screw fixed on the second end of the helix driver projecting away from the disk member aligned with the rotation axis and intermediate the first and second electrodes also for projecting engagement with the AVN fat pad;
whereby rotation about the rotation axis of a tool engagable with the tool reception feature causes rotation of the helix driver and therefore of the helical screw into the AVN fat pad and draws the disk member into conforming engagement with the outer surface of the AVN fat pad.

11. A medical electrical lead adapted to conduct electrical signals from an implantable or external electrical stimulator to a site of the heart and to conduct electrical signals of the heart from the site to the implantable or external electrical stimulator comprising:
an elongated lead body extending from a lead body distal end to a connector at the lead body proximal end for mechanical and electrical attachment to the electrical stimulator;
an electrically non-conductive disk member at the lead body distal end;
at least a first electrode fixed on the disk member and protruding therefrom for puncturing engagement with the epicardial surface of the heart in the region of an atrioventricular node (AVN) fat pad;
at least a second electrode fixed on the disk member, spaced from the first electrode, and protruding therefrom for puncturing engagement with the epicardial surface of the heart in the region of the AVN fat pad;
a first conductor extending from the first electrode to a first terminal of the connector; and
a second conductor extending from the second electrode to a second terminal of the connector
wherein the disk member includes a plurality of first parallel mutually spaced electrodes;
wherein the disk member includes a plurality of second parallel mutually spaced electrodes; and
wherein each of the first and second electrodes is elongated and extends to an angled tip end for ease of penetration into the fat pad.

12. A medical electrical lead adapted to conduct electrical signals from an implantable or external electrical stimulator to a site of the heart and to conduct electrical signals of the heart from the site to the implantable or external electrical stimulator comprising:
an elongated lead body extending from a lead body distal end to a connector at the lead body proximal end for mechanical and electrical attachment to the electrical stimulator;
an electrically non-conductive disk member at the lead body distal end;
at least a first electrode fixed on the disk member and protruding therefrom for puncturing engagement with the epicardial surface of the heart in the region of an atrioventricular node (AVN) fat pad;
at least a second electrode fixed on the disk member, spaced from the first electrode, and protruding therefrom for puncturing engagement with the epicardial surface of the heart in the region of the AVN fat pad;
a first conductor extending from the first electrode to a first terminal of the connector; and
a second conductor extending from the second electrode to a second terminal of the connector
wherein the disk member is of semi-rigid material and has contoured undersurface being engageable with a similarly contoured outer surface of the AVN fat pad region of the epicardial surface of the heart.

13. A medical electrical lead adapted to conduct electrical signals from an implantable or external electrical stimulator to a site of the heart and to conduct electrical signals of the heart from the site to the implantable or external electrical stimulator comprising:
an elongated lead body extending from a lead body distal end to a connector at the lead body proximal end for mechanical and electrical attachment to the electrical stimulator;
an electrically non-conductive disk member at the lead body distal end;
at least a first electrode fixed on the disk member and protruding therefrom for puncturing engagement with the epicardial surface of the heart in the region of an atrioventricular node (AVN) fat pad;
at least a second electrode fixed on the disk member, spaced from the first electrode, and protruding therefrom for puncturing engagement with the epicardial surface of the heart in the region of the AVN fat pad;
a first conductor extending from the first electrode to a first terminal of the connector; and
a second conductor extending from the second electrode to a second terminal of the connector
wherein the disk member includes a plurality of first parallel mutually spaced electrodes;
wherein the disk member includes a plurality of second parallel mutually spaced electrodes; and
wherein the disk member has a generally planar under surface from which the plurality of the first and second electrodes project; and
including:
at least one conductive plate mounted on the undersurface and electrically in continuity with the plurality of the first electrodes; and
at least one conductive plate mounted on the undersurface and electrically in continuity with the plurality of the second electrodes.

\* \* \* \* \*